United States Patent [19]

Balschmidt et al.

[11] Patent Number: 5,164,366

[45] Date of Patent: Nov. 17, 1992

[54] HUMAN INSULIN ANALOGUES

[75] Inventors: Per Balschmidt, Espergaerde; Jens J.V. Brange, Klampenborg, both of Denmark

[73] Assignee: Novo Nordisk A/S, Bagsvaerd, Denmark

[21] Appl. No.: 453,445

[22] Filed: Dec. 20, 1989

Related U.S. Application Data

[63] Continuation of Ser. No. 416,218, Oct. 2, 1989, abandoned, which is a continuation of Ser. No. 332,697, Apr. 3, 1989, abandoned.

[30] Foreign Application Priority Data

Dec. 23, 1988 [DK] Denmark .............................. 7215/88
Sep. 28, 1989 [DK] Denmark .............................. 4777/89

[51] Int. Cl.$^5$ ....................... C07K 7/40; A61K 37/26
[52] U.S. Cl. ........................................ 514/3; 530/303; 435/69.4
[58] Field of Search .......................... 530/303; 514/3; 435/69.4, 68.1

[56] References Cited

U.S. PATENT DOCUMENTS 3,903,069  9/1975  Geregory ........................... 530/303
4,320,196  3/1982  Morihara et al. ....................... 514/3
4,701,440  10/1987  Grau ..................................... 514/3

FOREIGN PATENT DOCUMENTS 0254516  1/1988  European Pat. Off. ................ 514/3
WO/8910937  11/1989  World Int. Prop. O. .............. 514/3

OTHER PUBLICATIONS

Frank, B., "Self-Assocation and Confermational Studies on Human Poinsulin and Insulin Analogs", Abstract, Conference on Insulin, 1989.
Chance, R., "Preparation of a New Series of Insulin Analogs", Conference on Insulin, Sep. 1989.
Nakagawa, S. et al., *Journal of Biological Chemistry*, 262(25): 12054–58, Sep. 1987.

Primary Examiner—Merrell C. Cashion, Jr.
Assistant Examiner—Susan M. Perkins
Attorney, Agent, or Firm—Steve T. Zelson

[57] ABSTRACT

The present invention relates to novel human insulin analogues exhibiting a low ability to associate in solution, a method for the preparation of such insulin analogues, insulin preparations containing the human insulin analogues of the invention and a method of treating Diabetes Mellitus using these human insulin analogues.

35 Claims, 5 Drawing Sheets

```
         10        20        30        40        50        60
          |         |         |         |         |         |
GAATTCCATTCAAGAATAGTTCAAACAAGAAGATTACAAACTATCAATTTCATACACAAT 70        80        90       100       110       120
          |         |         |         |         |         |
ATAAACGACCAAAAGAATGAAGGCTGTTTTCTTGGTTTTGTCCTTGATCGGATTCTGCTG
                  METLysAlaValPheLeuValLeuSerLeuIleGlyPheCysTrp 130       140       150       160       170       180
          |         |         |         |         |         |
GGCCCAACCAGTCACTGGCGATGAATCATCTGTTGAGATTCCGGAAGAGTCTCTGATCAT
AlaGlnProValThrGlyAspGluSerSerValGluIleProGluGluSerLeuIleIle 190       200       210       220       230       240
          |         |         |         |         |         |
CGCTGAAAACACCACTTTGGCTAACGTCGCCATGGCTAAGAGATTCGTTAACCAACACTT
AlaGluAsnThrThrLeuAlaAsnValAlaMETAlaLysArgPheValAsnGlnHisLeu 250       260       270       280       290       300
          |         |         |         |         |         |
GTGCGGTTCCCACTTGGTTGAAGCTTTGTACTTGGTTTGCGGTGAAAGAGGTTTCTTCTA
CysGlySerHisLeuValGluAlaLeuTyrLeuValCysGlyGluArgGlyPhePheTyr 310       320       330       340       350       360
          |         |         |         |         |         |
CACCAAGGCTGCTAAGGGTATTGTCGAACAATGCTGTACCTCCATCTGCTCCTTGTACCA
ThrLysAlaAlaLysGlyIleValGluGlnCysCysThrSerIleCysSerLeuTyrGln 370       380       390       400
          |         |         |         |
ATTGGAAAACTACTGCAGCTAGACGCAGCCCGCAGGCTCTAGA
LeuGluAsnTyrCysSer
```

HUMAN INSULIN ANALOGUES

This is a continuation of Ser. No. 07/416,218 filed Oct. 2, 1989 which is a continuation of Ser. No. 332,697 filed Apr. 3, 1989, both abandoned.

TECHNICAL FIELD

The present invention relates to novel human insulin analogues exhibiting a low ability to associate in solution, a method for the preparation of such insulin analogues, insulin preparations containing the human insulin analogues of the invention and a method of treating Diabetes Mellitus using these human insulin analogues.

BACKGROUND ART

Ever since the discovery of insulin in 1922 many different types of insulin preparations have been used for the treatment of Diabetes mellitus. At the beginning exclusively insulin solutions exhibiting a rapidly commencing and relatively rapidly ceasing insulin activity were used, but later on insulin preparations exhibiting a wider profile of activity procured by lowering the solubility of insulin by means of additions as e.g. zinc salt and/or protamines have been produced. For reasons of availability the insulin used herefor has normally been recovered from Pancreas from domestic animals, most frequently oxes, pigs and sheep, however, recently preparations containing human insulin of biotechnological origin have also appeared on the market.

The structure of human insulin is shown in the following formula

The insulins from certain domestic animals are very similar in structure to human insulin. Thus dog and pig insulin differ from human insulin only by containing Ala in position 30 in the B-chain and rabbit insulin only by containing Ser in the same position. These insulins may be converted into human insulin by replacement of the B30-amino acid residue with Thr by semisynthetic procedures as described by Morihara et al, Nature 280 (1979), 412-413 and Marcussen (U.S. Pat. No. 4,343,898).

When such an insulin is dissolved at physiological pH value a concentration-dependent association equilibrium is established between monomeric, dimeric, tetrameric, hexameric and even polymeric insulin. The equilibrium can e.g. be determined by ultracentrifugation, by osmometry or by gel filtration methods, vide e.g. R. Valdes Jr. and G. A. Ackers, "Methods in enzymology", vol. 61 (Enzyme Structure, part H. eds.; Hirs & Timasheff), Academic Press 1979, pages 125-142. In normal formulations of insulin preparations this equilibration is shifted in such a way that the insulin to a very high degree is on a hexameric form.

Substitutions in the insulin molecule can be introduced with the purpose of improving the profile of activity of the insulin in the treatment of Diabetes. Thus, Published International Application No. WO 86/05497 discloses that one or more substitutions of Glu in the insulin molecule by a neutral amino acid residue causes a shifting of the zone of precipitation of the insulin in such a way that a slow release after injection is obtained.

Moreover, Published European Application No. EP 214 826 discloses insulin analogues being particularly rapidly absorbed after injection. This effect is a result of the fact that by means of certain substitutions in particular in the B9-B12 region and in the B26-B28 positions in the insulin molecule a suppression of the association tendency of the insulin is obtained so that it is essentially present as monomer or dimer. However, a number of these insulin analogues exhibits a reduced biological activity.

Throughout the years a large number of artificially prepared analogues of human insulin has been described, usually with the purpose of elucidating the influence of the structure on the activity, vide e.g. Märke et al., Hoppe-Seyler's Z. Physiol Chem. 360 (1979), 1619-1632. Investigations of the influence of substitutions in the (B22-B26)-sequence of the insulin on the receptor binding have been of particular interest, as said sequence is considered to be an essential site of binding for the insulin receptor, and as naturally occurring mutations have been found with substitutions in said site. Vide e.g. S. Shoelson et al. PNAS 80 (1983), 7390-7394 and M. Kobayashi et al.: Biomed. Res. 5 (3) (1984), 267-272. Very low biological activities were found for analogues in which Phe (B24) or Phe (B25)

are substituted, and therefore it was concluded that the presence of these two amino acids is of decisive importance to the receptor binding The present invention is based on the surprising recognition that certain human insulin analogues in which one of the amino acid residues [Phe$^{B24}$] or [Phe$^{B25}$] is not present exhibit a low association tendency in solution and at the same time exhibits an unchanged or even higher in vitro biological activity than human insulin. The deletion of either [Phe$^{B24}$] or [Phe$^{B25}$] will have the effect that [Lys$^{B29}$] is transferred into [Lys$^{B28}$]. The position of a positive charge in this position in the human insulin molecule is considered to be the important aspect of the present invention.

SUMMARY OF THE INVENTION

In its broadest aspect the present invention is therefore related to human insulin analogues in which there is a positively charged amino acid residue, i.e. Lys or Arg in the position B28, i.e. in position 8 in the B-chain calculated from [Gly$^{B20}$].

The present insulin analogues have surprisingly a low association tendency and at the same time an increased physical stability compared to other insulin analogues with low association tendency. Introduction of a positive charge in position B28 may be accomplished in two ways. Either by deleting one of the amino acid residues in position B24, B25, B26, B27 or B28 in the human insulin molecule leading to a human insulin analogue with a Lys in position B28 or by substituting [Pro$^{B28}$] the human insulin molecule with a Lys or Arg. If an Arg is preferred in position B28 the deletion of one of the amino acid residues in position B24, B25, B26, B27 or B28 may furthermore be combined with a substitution of the original [Lys$^{B29}$] with an Arg residue.

The present human insulin analogues may furthermore contain one or more modifications in the C-terminal end of the B-chain compared to human insulin. Thus, the amino acid residues in position B25 to B27 and the amino acid residue(s) following the [Lys$^{B28}$] or [Arg$^{B28}$] may be arbitrarily chosen among the naturally occurring amino acid residues or B29 or B30 or both may be lacking.

According to one aspect of the present invention [Tyr$^{B26}$] may be substituted by another uncharged amino acid residue wherein the second carbon atom in the side chain (C$\gamma$) is sp$^2$-hybridized (the bonds having a planar structure).

Also with the purpose of stabilizing the molecule against chemical degradation, Asn in position A21 and/or B3 may furthermore be replaced by another amino acid residue.

The present human insulin analogues can be characterized by the following formula I wherein $X_1$, $X_2$, $X_3$, $X_5$, $Y_1$ and $Y_2$ may be any naturally occurring amino acid residue, $X_4$ is Lys or Arg, $X_6$ may be any naturally occurring amino acid residue carrying the C-terminal hydroxy group or —OH or $X_5$ and $X_6$ together form the C-terminal hydroxy group.

In an embodiment of the invention $X_5$ is selected from the group consisting of any naturally occurring amino acid residue except Pro.

In the above formula $Y_1$ and/or $Y_2$ may in one embodiment be selected from the group consisting of any naturally occurring amino acid residue except Asn.

In the above formula I $X_1$ may more specifically be Phe, Ala, His, Thr, Ser, Asn or Tyr, $X_2$ may more specifically be Tyr, Thr, Glu, Asp, Ala, His, Ser or Phe, $X_3$ may more specifically be Pro, Glu, Asp, Ser, Thr or His, $X_5$ may more specifically be Lys, Thr, Ser, Ala, Asp or Glu, $X_6$ may more specifically be Thr-OH, Ser-OH, Ala-OH, Asp-OH, Glu-OH or —OH, $Y_1$ may be Asn, Glu, Asp, His, Ser, Thr, Val, Leu, Ile, Ala, Met, Trp, Tyr, Gln or Gly, more preferably Gly, Asp, Glu or Ala, and $Y_2$ may be Asn, Glu, Asp, His, Ser, Thr, Val, Leu, Ile, Ala, Met, Trp, Tyr, Gln or Gly, more preferably Glu or Asp.

One group of the present human insulin analogues can be characterized as such in which one of the amino acid residues in position B24 or B25 has been deleted, that the amino acid residue in position B26, optionally, is substituted by another uncharged amino acid residue in which the carbon atom in the $\gamma$-position is sp$^2$-hybridized, that, optionally, one or more of the amino acid residues in positions A21, B3 and B30 differ from the amino acid residue in the corresponding positions in human insulin, and that, optionally, no amino acid residue is present in position B30.

According to a more simple definition such analogues are human insulin analogues in which [Tyr$^{B26}$] is not present, in which [Phe$^{B25}$] has optionally been substituted by another uncharged amino acid residue in which the carbon atom in the γ-position is sp$^2$-hybridized, in which one or more of the amino acid residues in positions A21, B3 and B30, optionally, differ from the amino acid residues in human insulin and in which optionally no amino acid residue is present in position B30.

Examples of uncharged amino acid residues in which $C_\gamma$ is sp$^2$-hybridized are Tyr, Phe, His, Trp and Asn.

It is possible to introduce further substitutions or derivatizations in the human insulin analogues mentioned above if the properties do not change substantially. Such further derivatizations could be esterification or amidation of carboxyl groups, acylation or alkylation of amino- or hydroxyl groups or could be deamidation of carboxamide groups. Further substitutions maybe exchange of [Thr$^{A8}$] with His or of [His$^{B10}$] with Asp. Moreover, it is possible to add or delete a single or a few amino acid residues at the C- and/or the N-terminal of preferably the B-chain.

One group of the human insulin analogues according to the invention will have the structure shown in formula II below, where X means Tyr, His, Phe or Asn, Y means Thr, Ser, Ala, Asp or Glu or a deletion and where optionally one or both of the underscored Asn have been changed to Asp by substitution or deamidation or the underscored Asn in the A-chain may be Gly.

[Asp$^{A21}$]-des[Phe$^{B25}$],des[Thr$^{B30}$]-human insulin
[Asp$^{B28}$]-des[Phe$^{B25}$]-human insulin
[Asp$^{B3}$]-des[Phe$^{B25}$]-human insulin
[Lys$^{B28}$]-human insulin
[Lys$^{B28}$,Thr$^{B29}$]-human insulin
[Arg$^{B28}$]-des[Lys$^{B29}$]-human insulin The human insulin analogues according to the present invention may advantageously be used in the treatment of Diabetes as the decreased ability to association leads to a faster uptake in the bloodstream than an ordinary insulin not only after the normally used subcutaneous injection but also by non-parenteral use, vide e.g. Published International Application No. WO87/06137. Also their improved physical stability will make them more advantagous in the Diabetes treatment.

The insulin analogues according to the present invention may be prepared by altering the proinsulin gene through replacement of codon(s) at the appropriate site in the native human proinsulin gene by codon(s) encoding the desired amino acid residue substitute(s) and/or by deleting the codon(s) corresponding to the desired deletion(s). Alternatively, the whole DNA-sequence encoding the desired insulin analogue may be synthesized. The gene encoding the desired insulin analogue is then inserted into a suitable expression vector which when transferred to a suitable host organism, e.g. *E. coli*, Bacillus or yeast, generates the desired product. The expressed product is then isolated from the cells or the culture broth depending on whether the expressed product is secreted from the cells or not.

Preferred human insulin analogues according to the invention are the following:
des[Phe$^{B25}$]-human insulin
des[Tyr$^{B26}$]-human insulin
des[Thr$^{B27}$]-human insulin
des[Pro$^{B28}$]-human insulin
des[Phe$^{B25}$]-porcine insulin
des[Pro$^{B28}$]-porcine insulin
des[Pro$^{B28}$]-rabbit insulin
des[Phe$^{B25}$],des[Thr$^{B30}$]-human insulin
des[Tyr$^{B26}$],des[Thr$^{B30}$]-human insulin
[Ser$^{A21}$]-des[Pro$^{B28}$]-human insulin
[Gly$^{A21}$]-des[Pro$^{B28}$]-human insulin
[Gly$^{A21}$]-des[Phe$^{B25}$]-human insulin
[Asp$^{A21}$]-des[Phe$^{B25}$]-human insulin
[His$^{B25}$]-des[Tyr$^{B26}$],des[Thr$^{B30}$]-human insulin
[Asn$^{B25}$]-des[Tyr$^{B26}$],des[Thr$^{B30}$]-human insulin The novel insulin analogues may also be prepared by chemical synthesis by methods analogue to the method described by Märki et al. (Hoppe-Seyler's Z. Physiol. Chem., 360 (1979), 1619–1632). They may also be formed from separately in vitro prepared A- and B-chains containing the appropriate amino acid residue substitutions and deletions, whereupon the modified A- and B-chains are linked together by establishing disulphide bridges according to known methods (e.g. Chance et al., In: Rick DH, Gross E (eds) Peptides: Synthesis—Structure—Function. Proceedings of the seventh American peptide symposium, Illinois, pp. 721–728).

The insulin analogues may furthermore be prepared by a method analogue to the method described in EP patent application No. 0163529A, the disclosure of which is incorporated by reference hereinto. By such method an insulin precursor of the human insulin analogue wherein the basic amino acid in position B28 or B29 (if the final product shall have a basic amino acid in this position) is connected to Gly$^{A1}$ by means of either a peptide bond or a peptide chain of varying length is expressed and secreted by yeast with correctly positioned disulphide bridges and is then converted into the desired human insulin analogue by the Morihara method (Morihara supra) or the so-called transpeptidation reaction (see U.S. Pat. No. 4,343,898).

Accordingly the present insulin analogues may be prepared by inserting a DNA-sequence encoding a precursor of the insulin analogue in question into a suitable yeast expression vehicle which when transferred to yeast is capable of expressing and secreting the precursor of the insulin analogue in which [Lys$^{B28}$], [Arg$^{B28}$], [Lys$^{B29}$] or [Arg$^{B29}$] is connected to Gly$^{A1}$ by a peptide bond or a peptide chain with the formula III $$-R_n-R^1- \qquad (III)$$

wherein R is a peptide chain with n amino acid residues, n is an integer from 0 to 33 and R$^1$ is Lys or Arg when culturing the transformed yeast strain in a suitable nutrient medium. The precursor is then recovered from the culture broth and reacted with an amino compound with the formula IV $$Q-OR'' \qquad (IV)$$

wherein Q is a single amino acid residue, preferably Thr, or a dipeptide, and R'' is a carboxy protecting group (e.g. methyl or tert-butyl), using trypsin or trypsin-like enzyme as a catalyst in a mixture of water and organic solvents analogously as described in U.S. Pat. No. 4,343,898 (the disclosure of which is incorporated by reference hereinto) whereupon the carboxy protecting group is removed and the insulin analogue is isolated from the reaction mixture.

If the insulin analogues contain an amino acid residue different from Lys or Arg as the C-terminal residue in the B-chain, they may also be prepared by a method analogue to the method described in Published European Application No. EP 195 691 the disclosure of which is incorporated by reference hereinto. By this method insulin analogue precursors of the type having a bridge between the A- and B-chain consisting of a single pair of basic amino acid (Lys, Arg) are made in yeast and then converted into the insulin analogue by an enzymatic conversion.

If the C-terminal amino acid residue in the B-chain is Lys or Arg, then the insulin analogues can be prepared from the above biosyntetic precursors by enzymatic cleavage with trypsin.

Human insulin analogues of the invention in which substitutions are only present within the last amino acid residues nearest to the C-terminal of the B-chain may moreover be prepared in a manner known per se from e.g. porcine insulin as described in K. Inoye et al.; JACS 101 (3), (1979), 751-752, whereby the porcine insulin is first split with trypsin to des-(B23-30)-human insulin, whereupon the latter, also enzymatically, is coupled with a synthetic peptide having the desired amino acid sequence.

The present insulin analogues may be used for the preparation of novel insulin preparations with insulin activity to be substituted for human or porcine insulin in the insulin preparations heretofore known to the art. Such novel insulin preparations contain the insulin analogues according to the present invention or a pharmaceutically acceptable salt thereof in aqueous solution or suspension, preferably at neutral pH. The aqueous medium is made isotonic, for example with sodium chloride, sodium acetate or glycerol. Furthermore, the aqueous medium may contain zinc ions, buffers such as acetate and citrate and preservatives such as m-cresol, methylparaben or phenol. The pH value of the preparation is adjusted to the desired value and the insulin preparation is made sterile by sterile filtration.

The present insulin analogues may also be mixed with other insulin analogues having a protracted insulin activity to prepare insulin preparations consisting of a mixture of rapid acting and protracted insulin.

The insulin preparations of this invention can be used similarly to the use of the known insulin preparations.

TERMINOLOGY

The abbreviations used for the amino acids are those stated in J. Biol. Chem. 243 (1968), 3558. The amino acids are in the L configuration. Unless otherwise indicated, the species of insulins stated herein is human.

BRIEF DESCRIPTION OF THE DRAWINGS

The invention is further illustrated with reference to the accompanying drawings in which.

DETAILED DESCRIPTION

Figure 1:
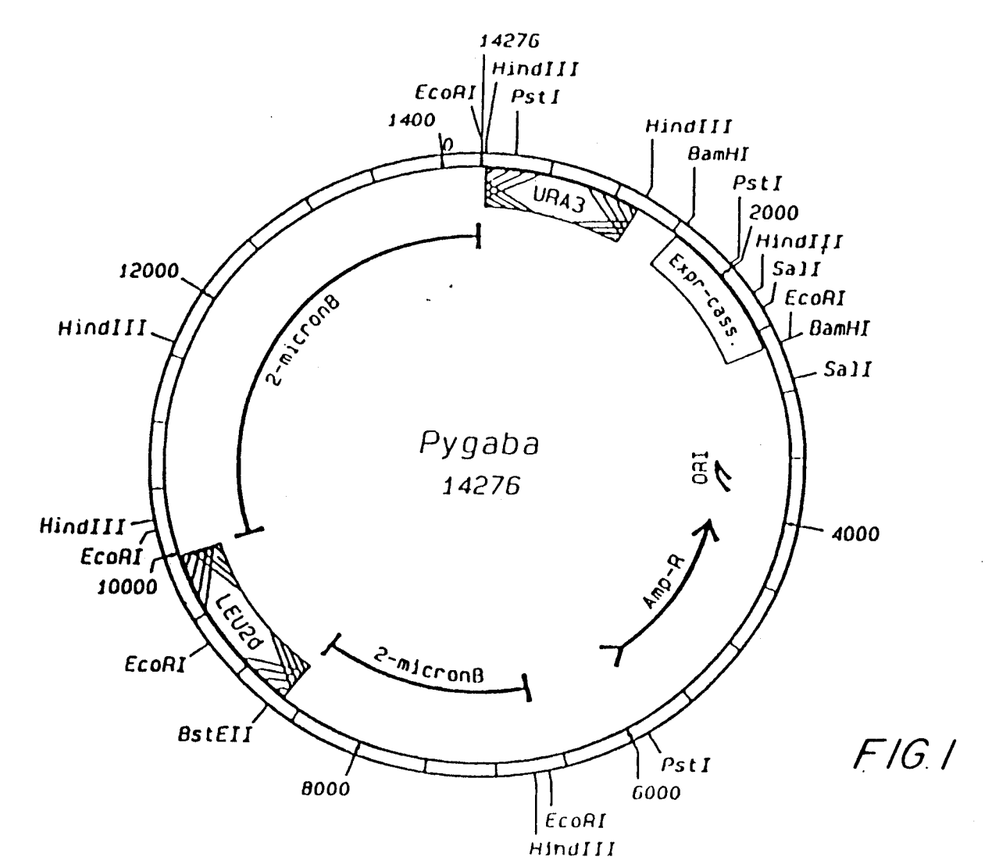
FIG. 1 shows the expression plasmid pYGABA 14276.

DNA-sequences encoding modified insulin precursors were constructed with basis in the expression cassette, which is contained in the BamHI restriction fragment from the expression plasmid pYGABA as shown in FIG. 1, has a lenght of 1103 basepairs and contains essentially the following (listed in succession starting from the 5'-end): The GAPDH promoter (Travis et al., J. Biol. Chem., 260 (1985), 4384-4389) followed by the coding region consisting of: The 83 N-terminal amino acids of the MF α1-leader sequence encoded by the wild-type yeast DNA-sequence as described by Kurjan & Herskowitz followed by the two codons AAA and AGA encoding Lys and Arg and again followed by the coding region for the insulin precursor single chain des [Thr$^{B30}$]- human insulin (SCI), which is a synthetically constructed gene using preferred yeast codons. After two stop-codons, a SalI restriction site is positioned, and the rest of the sequence constitutes the MFα1-sequence containing the terminator region. The sequence is constructed using entirely standard techniques.

The method employed was "oligonucleotide site directed mutagenesis", which is described by Zoller & Smith, DNA, Vol. 3, No. 6 (1984), 479-488. The method is briefly described in the following, and is described thoroughly in Example 1. The insulin precursor sequence is isolated from the expression plasmid and inserted into a single-stranded genom, circular M13 bacteriophage vector. A chemically synthesized complementary DNA-strand is then annealed to the single-stranded genom. The DNA-strand contains the desired sequence surrounded by sequences completely homologous to insulin sequences on the circurlar DNA. The primer is then extended in vitro into the entire length of the circular genom biochemically using Klenow polymerase. This strand will give rise to single-stranded phages, which when grown in *E. coli* give the possibility of isolating double-stranded DNA with the desired sequence. From this double-stranded DNA, a restriction fragment can be isolated and reinserted into the expression vector.

MODES FOR CARRYING OUT THE INVENTION

The invention is further illustrated by the following Examples.

EXAMPLE I

Construction of an expression plasmid, which can be used to express des[Phe$^{B25}$]-SCI.

The expression cassette, which is contained in the expression plasmid pYGABA (shown in FIG. 1) on a BamHI restriction fragment, was isolated: The expression plasmid was incubated with the restriction endonuclease BamHI. The conditions were: 20 µg of plasmid, 50 units of BamHI, 100 mM NaCl, 50 mM TrisHCl, pH 7.5, 10 mM MgCl$_2$, and 1 mM DTT in a volume of 100 µliters. The temperature was 37° C. and the reaction time 2 hours. The two DNA-fragments were separated on a 1% agarose gel, and the desired fragment was isolated.

Ligation to the M13 vector M13mp18:

The isolated restriction fragment was ligated to the bacteriophage vector M13mp18 also cut with the restriction endonuclease BamHI in the following reaction mixture: Fragment 0.2 µg, vector 0.02 µg, 50 mM Tris-HCl, pH 7.4, 10 mM MgCl$_2$, 10 mM DTT and 1 mM ATP in a volume of 20 µliters. 5 µliters of this mixture were transformed into the *E. coli* strain JM101. The presence of fragment in the vector and the orientation of the fragment was determined by restriction enzyme mapping on double-stranded M13-DNA isolated from the transformants.

Isolation of single-stranded (ss) DNA (template):

From the transformant described above ss-DNA was isolated according to a method described by Messing in Gene, 19 (1982), 269–276.

5'phosohorylation of the mutaqenisation primer:

The mutagenisation primer with the sequence 5'-TTGGAGTGTAGAAACCTCTT-3' was phosphorylated in the 5'-end in a 30 µliters reaction mixture containing 70 mM Tris-HCl, pH 7.0, 10 mM MgCl$_2$, 5 mM DTT, 1 mM ATP, 100 pmol oligonucleotide and 3.6 units of T4 polynucleotide kinase. The reaction was carried out for 30 min. at 37° C. Then, the enzyme was inactivated by incubating the mixture for 10 min. at 65° C.

Annealing of template and phosphorylated mutagenisation primer:

Annealing of template and primer was carried out in a 10 µliters volume containing 0.5 pmol template, 5 pmol primer, 20 mM Tris-HCl, pH 7.5, 10 mM MgCl$_2$, 50 mM NaCl and 1 mM DTT by heating for 10 min. at 65° C. and cooling afterwards to 0° C.

Extension/ligation reaction:

To the reaction mixture above, 10 µliters of the following mixture were added: 0.3 mM dATP, 0.3 mM dCTP, 0.3 mM dGTP, 0.3 mM TTP, 1 mM ATP, 20 mM Tris-HCl, pH 7.5, 10 mM MgCl$_2$, 10 mM DTT, 3 units of T4 DNA ligase and 2.5 units of Klenow polymerase. Then, the reaction was carried out for 16 hours at 16° C.

Transformation of JM101:

The reaction mixture above was transformed in different dilutions into CaCl$_2$-treated *E. coli* JM101 cells using standard techniques and plated in 2×YT topagar on 2×YT agar plates. (2×YT=tryptone 16 g/liter, yeast extract 10 g/liter, NaCl 5 g/liter. 2×YT topagar=2×YT with 0.4% agarose added and autoclaved. 2×YT agar plates=2×YT with 2% agar added and autoclaved). The plates were incubated at 37° C. overnight.

Identification of positive clones:

The method used was plaque-lift hybridisation which is described in the following: a nitrocellulose-filter was placed on a plate with a suitable plaque-density, so that the filter was wetted. The filter was then bathed in the following solutions: 1.5 M NaCl, 0.5M NaOH for 30 sec., 1.5 M NaCl, 0.5M Tris-HCl, pH 8.0 for 1 min., 2×SSC (0.3 M NaCl, 0.03M sodium citrate) till later use. The filter was dried on 3MM filter paper and baked for 2 hours at 80° C. in a vacuum oven.

The mutagenisation primer with the sequence 5'TTGGAGTGTAGAAACCTCTT-3' was labelled radioactively in the 5' end in a 30 µliters volume containing 70 mM Tris-HCl, pH 7.5, 10 mM MgCl$_2$, 5 mM DTT, 10 pmol oligonucleotide, 20 pmol γ-$^{32}$P-ATP and 3.5 units of T4 polynucleotide kinase. The mixture was incubated at 37° C. for 30 min. and then for 5 min. at 100° C.

The dried filter was prehybridised for 2 hours at 65° C. in 6×SSC, 0.2% bovine-serum albumin, 0.2% Ficoll, 0.2% polyvinylpyrrolidon, 0.2% sodium-dodecyl-sulphate (SDS) and 50 µg/ml salmon-sperm DNA. Then, the reaction mixture containing the labelled probe was added to 15 ml of fresh prehybridisation mix, and the filter was bathed herein overnight at 28° C. with gentle shaking. After hybridisation the filter was washed 3 times for each 15 min. in 2×SSC+0.1% SDS and autoradiographed. After wash in the same solution, but now at 52° C., and another autoradiography, plaques containing DNA-sequences complementary to the mutagenisation primer were identified.

Re-screening of positive clones:

Because the identified clone is a result of a heteroduplex, the plaque was plated again. The hybridisation and identification were repeated.

Purification of double-stranded M13-phage DNA:

A re-screened clone was used for infection of the *E. coli* strain JM101. A culture containing approximately 10$^8$ phages and 5 colonies of JM101 was grown for 5 hours in a 5 ml 2×YT medium at 37° C. Then, double-stranded, circular DNA was purified from the pellet according to a method described by Birnboim & Doly, Nucleic Acids Res., 2 (1979), 1513.

Isolation of a restriction fragment containing modified insulin precursor:

The DNA-preparation (appr. 5 µg) isolated above was digested with 10 units of the restriction endonuclease BamHI in 60 µliters of 100 mM NaCl, 50 mM Tris-HCl, pH 7.5, 10 mM MgCl$_2$, and 1 mM DTT for 2 hours at 37° C. The DNA-products were separated on an agarose-gel, and the fragment was purified from the gel.

Figure 2:
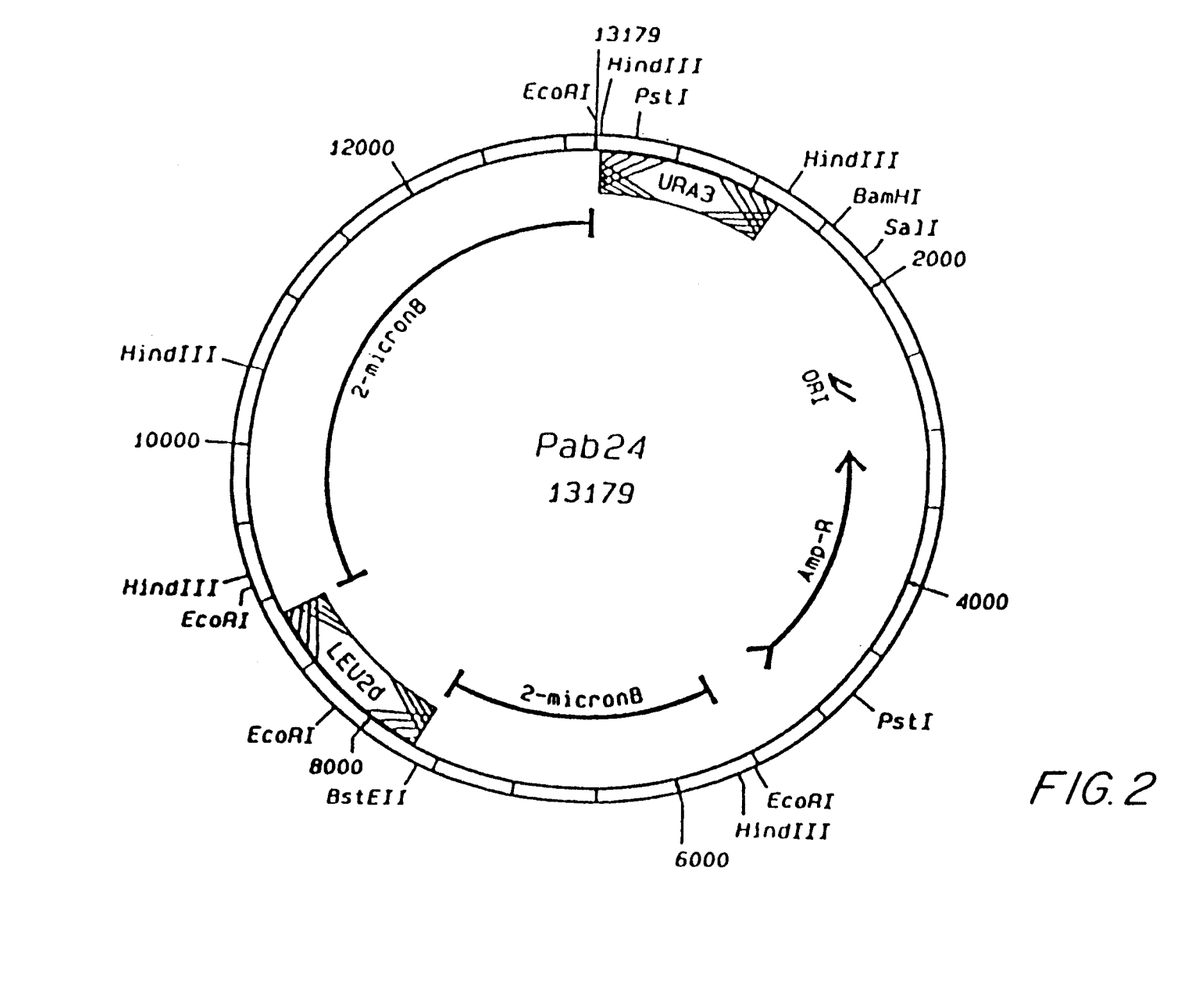
FIG. 2 shows the yeast vector pAB24.

Ligation to the yeast vector pAB24 (FIG. 2):

The isolated restriction fragment was ligated to the yeast vector pAB24 digested with the restriction endonuclease BamHI in the following reaction mixture: Fragment 0.2 µg, vector 0.02 µg, 50 mM Tris-HCl, pH 7.4, 10 mM MgCl$_2$, 10 mM DTT, 1 mM ATP in a total volume of 20 μliters. 5 μliters of this reaction mix was used for transformation of the *E. coli* strain MC1061, in which the modified expression plasmid was identified and propagated. The plasmid was identical to pYGABA, except for the deleted codon.

Transformation of yeast:

Transformation of the expression plasmid into the yeast strain *Saccharomyces cerevisiae* JC482ΔpepΔLeu2-cir° (α, his4, pep4, ura3, leu2, cir≧) was carried out as described by Ito et al., J. Bact., Vol. 153, No. 1, (1983), 163–168. The transformed cells were plated on SC-ura medium (0.7% Yeast Nitrogen Base, 2.0% glucose, 0.5% casamino acids, 2.0% agar) for selection for plasmid-containing cells.

EXAMPLE II

Construction of an expression plasmid, which can be used for production of des[Tyr$^{B26}$]-SCI.

The procedure used was essentially the same as described in example I, except that the mutagenisation primer had the sequence 5'-ACCCTTTGGAGT-GAAGAAACCTCT-3', that the hybridization temperature was 36° C., and that the washing temperature after hybridization was 60° C. The modified plasmid has a sequence identical to pYGABA, except for the deleted codon.

EXAMPLE III

Construction of an expression plasmid, which can be used for production of [His$^{B25}$],des[Tyr$^{B26}$]-SCI.

The procedure used was essentially the same as described in example I, except that the mutagenisation primer had the sequence 5'-AATACCCTTT-GGAGTGTGGAAACCTCTTTCACC-3', that the hybridization temperature was 43° C., and that the washing temperature after hybridization was 66° C. The modified plasmid has a sequence identical to pYGABA, except for the modified and deleted codons.

EXAMPLE IV

Construction of an expression plasmid, which can be used for production of [Asn$^{B25}$],des[Tyr$^{B26}$]-SCI.

The procedure used was essentially the same as described in example I, except that the mutagenisation primer had the sequence 5'-AATACCCTTT-GGAGTGTTGAAACCTCTTTCACC-3', that the hybridization temperature was 42° C., and that the washing temperature after hybridization was 65° C. The modified plasmid has a sequence identical to pYGABA, except for the modified and deleted codons.

EXAMPLE V

Expression of precursor and isolation from the culture medium.

Yeast, transformed as described in examples I to IV, was propagated on Petri-plates containing minimal-medium without u-racil for 48 hours at 30° C. 100 ml shake bottles containing minimal-medium without uracil+5 g/liter casamino acids +10 g/liter succinic acid+30 g/liter glucose at pH 5.0 was inoculated with a single colony from the Petri-plate. The bottles were then shaken at 30° C. in incubator for 72 hours.

After centrifugation 1 liter of pooled supernatant was sterilized by filtration and adjusted to pH 4–4.5 and a conductivity <10 mS by addition of 5M HCl and water. With a flow of 120 ml/hour the supernatant was then applied to a 1.6×6 cm column of S/Sepharose®FF previously equilibrated with 50 mM acetic acid, 50% (by volume) ethanol adjusted to pH 4.0 with NaOH. The column was washed with 60 ml buffer and the precursor was then eluted by a linear gradient of NaCl from 0 to 0.35M in 360 ml buffer with a flow of 10 ml/hour. The eluate was divided in fractions of 4 ml and detected for UV-absorbance. Fractions containing precursor were identified by RP-HPLC analysis and were pooled. After desalting on a column of Sephadex®G25 in 1M acetic acid the precursor was isolated by lyophilization.

EXAMPLE VI

Preparation of des[Phe$^{B25}$],des[Thr$^{B30}$]-human insulin.

400 mg of des[Phe$^{B25}$]-SCi, prepared by the methods described in examples I and V, were dissolved in 40 ml of 50 mM tris(hydroxymethyl)aminomethane, 20% (by volume) ethanol adjusted to pH 9 with HCl and 40 ml (settled volume) of Sepharose® containing 32 mg of immobilized trypsin in the same buffer were added. The suspension was left for 24 hours at 8°–10° C. with gentle agitation and was then filtered. The gel was washed with 40 ml of buffer, and the pooled filtrates were applied to a 2.6×7.5 cm column of Q-Sepharose®FF previously equilibrated with 50 mM tris-(hydroxymethyl)aminomethane, 50% (by volume) ethanol, adjusted to pH 8.0 with HCl. The column was then eluted with a linear gradient of NaCl from 0 to 0.15M in the same buffer over 6 hours with a flow of 225 ml/hour. The eluate was detected for UV-absorbance and fractions containing the main protein peak were pooled. The protein was precipitated at pH 5.4 after removal of the ethanol in vacuo.

250 mg of des[Phe$^{B25}$],des[Thr$^{B30}$]-human insulin were isolated by lyophilization.

The identity of the product was confirmed by amino acid analysis, by plasma desorption mass spectrometry and by sequential Edman degradation of the separated vinylpyridylated A- and B-chains.

EXAMPLE VII

Preparation of des[Phe$^{B25}$]-human insulin.

200 mg of des[Phe$^{B25}$],des[Thr$^{B30}$]-human insulin prepared by the methods described in example VI were dissolved in a mixture containing 400 mg of threonine methyl ester, 2.0 ml of ethanol and 0.8 ml of water. The pH value was adjusted to 6.3 with acetic acid and 4 ml (settled volume) of Sepharose® containing 3.2 mg of immobilized trypsin were added. After standing for 2 hours at 20° C. with gentle agitation, the gel was removed by filtration, and the protein was precipitated by addition of 10 volumes of 2-propanol. The air-dried precipitate was redissolved in 20 mM tris(hydroxymethyl)aminomethane/HCl, 60% (by volume) ethanol, pH 8.25, and applied to a 2.6×20 cm Q-Sepharose®FF column, previously equilibrated with the said buffer, and eluted with a linear NaCl-gradient in the same buffer increasing from 0 to 0.1M over 15 hours at a flow rate of 125 ml/hour. The ethanol was removed in vacuo from the pooled fractions containing des [Phe$^{B25}$]-human insulin-(B30-methyl ester), and the protein was precipitated at pH 6.1. The suspension was centrifugated and the precipitate was lyophilized. The methyl ester was then hydrolyzed for 10 min. in cold 0.1M NaOH at a protein concentration of 10 mg/ml. The reaction was stopped by adjusting the pH value to 8.5, and 2 volumes of 20 mM tris(hydroxymethyl)- aminomethane/HCl, pH 8.5, were added. The solution was then applied to a 2.6×20 cm Q-Sepharose ®FF column and eluted as described above. The protein was precipitated at pH 5.5 after removal of the ethanol in vacuo.

80 mg of des[Phe$^{B25}$]-human insulin were obtained after lyophilization.

The identity of the product was confirmed by amino acid analysis, by plasma desorption mass spectrometry and by sequential Edman degradation of the separated vinylpyridylated A- and B-chains.

EXAMPLE VIII

Preparation of des[Tyr$^{B26}$],des[Thr$^{B30}$]-human insulin.

250 mg of des[Tyr$^{B26}$]-SCI, prepared by the methods described in the examples II and V, were dissolved in 25 ml of 50 mM tris(hydroxymethyl)aminomethane, 20% (by volume) ethanol adjusted to pH 9 with HCl and 25 ml (settled volume) of Sepharose ® containing 20 mg of immobilized trypsin in the same buffer were added. The suspension was left for 24 hours at 8°-10° C. with gentle agitation and was then filtered. The gel was washed with 25 ml of buffer, and the pooled filtrates were applied to a 2.6×7.5 cm column of Q-Sepharose ®FF previously equilibrated with 50 mM tris-(hydroxymethyl)aminomethane, 50% (by volume) ethanol, adjusted to pH 8.0 with HCl. The column was then eluted with a linear gradient of NaCl from 0 to 0.15M in the same buffer over 6 hours with a flow of 225 ml/hour. The eluate was detected for UV-absorbance and fractions containing the main protein peak were pooled. The protein was precipitated at pH 5.4 after removal of the ethanol in vacuo.

130 mg of des[Tyr$^{B26}$],des[Thr$^{B30}$]-human insulin were isolated by lyophilization.

The identity of the product was confirmed by amino acid analysis and by sequential Edman degradation of the separated vinylpyridylated A- and B-chains.

EXAMPLE IX

Preparation of [His$^{B25}$],des[Tyr$^{B26}$],des[Thr$^{B30}$]-human insulin.

450 mg of [His$^{B25}$],des[Tyr$^{B26}$]-SCI, prepared by the methods described in the examples III and V, were dissolved in 45 ml of 50 mM tris-(hydroxymethyl)aminomethane, 20% (by volume) ethanol adjusted to pH 9 with HCl and 45 ml (settled volume) of Sepharose ® containing 36 mg of immobilized trypsin in the same buffer were added. The suspension was left for 24 hours at 8°-10° C. with gentle agitation and was then filtered. The gel was washed with 40 ml of buffer, and the pooled filtrates were applied to a 2.6×7.5 cm column of Q-Sepharose ®FF previously equilibrated with 50 mM tris(hydroxymethyl)aminomethane, 50% (by volume) ethanol, adjusted to pH 8.0 with HCl. The column was then eluted with a linear gradient of NaCl from 0 to 0.15M in the same buffer over 6 hours with a flow of 225 ml/hour. The eluate was detected for UV-absorbance and fractions containing the main protein peak were pooled. The protein was precipitated at pH 5.4 after removal of the ethanol in vacuo.

200 mg of [His$^{B25}$],des[Tyr$^{B26}$],des[Thr$^{B30}$]-human insulin were isolated by lyophilization.

The identity of the product was confirmed by amino acid analysis and by sequential Edman degradation of the separated vinylpyridylated A- and B-chains.

EXAMPLE X

Preparation of [Asn$^{B25}$],des[Tyr$^{B26}$],des[Thr$^{B30}$]-human insulin.

150 mg of [Asn$^{B25}$],des[Tyr$^{B26}$]-SCI, prepared by the methods described in the examples IV and V, were dissolved in 15 ml of 50 mM tris-(hydroxymethyl)aminomethane, 20% (by volume) ethanol adjusted to pH 9 with HCl and 15 ml (settled volume) of Sepharose ® containing 12 mg of immobilized trypsin in the same buffer were added. The suspension was left for 24 hours at 8°-10° C. with gentle agitation and was then filtered. The gel was washed with 40 ml of buffer, and the pooled filtrates were applied to a 1.6×10 cm column of Q-Sepharose ®FF previously equilibrated with 50 mM tris(hydroxymethyl)aminomethane, 50% (by volume) ethanol, adjusted to pH 8.0 with HCl. The column was then eluted with a linear gradient of NaCl from 0 to 0.15 in the same buffer over 6 hours with a flow of 90 ml/hours. The eluate was detected for UV-absorbance and fractions containing the main protein peak were pooled. The protein was precipitated at pH 5.4 after removal of the ethanol in vacuo.

80 mg of [Ans$^{B25}$],des[Tyr$^{B26}$],des[Thr$^{B30}$]-human insulin were isolated by lyophilization.

The identity of the product was confirmed by amino acid analysis and by sequential Edman degradation of the separated vinylpyridylated A- and B-chains.

EXAMPLE XI

Preparation of [Asp$^{A21}$],des[Phe$^{B25}$],des[Thr$^{B30}$]-human insulin.

50 mg of des[Phe$^{B25}$],des[Thr$^{B30}$]-human insulin prepared by the methods described in example VI were dissolved in 10 ml water by adjusting the pH value to 2 with 1M HCl. The solution was then left for 16 days at 30° C. After cooling (to 20° C.) 7.5 g of urea were added and the pH value was adjusted to 8.1 with 1M NaOH. The solution was then applied to a 1.6×20 cm Q-Sepharose ®FF column, previously equilibrated with 20 mM tris(hydroxymethyl)-aminomethane/HCl, 7M urea, pH 8.1 at 4° C., and eluted with a linear NaCl-gradient in the same buffer increasing from 0 to 0.05M over 24 hours at a flow rate of 40 ml/hour. The pooled fractions containing the protein from the last eluting peak were desalted on a column of Sephadex ®G25 in 1M acetic acid and lyophilized.

30 mg of [Asp$^{A21}$],des[Phe$^{B25}$],des[Thr$^{B30}$]-human insulin were obtained.

The identity of the product was confirmed by amino acid analysis, by 5-step Edman degradation and by C-terminal analysis using carboxypeptidase A.

EXAMPLE XII

Preparation of [Ser$^{A1}$],des[Pro$^{B28}$]-human insulin.

Construction of an expression plasmid which can be used for production of [Ser$^{A21}$,des[Pro$^{B28}$]-human insulin and preparation of [Ser$^{A21}$,des[Pro$^{B28}$]-human insulin.

A pUC-19 derived plasmid, pKFN-864, encoding this analogue was constructed by gapped duplex mutagenesis (Y. Morinaga et al., Biotechnology 2 (1984), 636-639) of plasmid pKFN-734 using the two mutagenic primers NOR-648 CTA-GAGCCTGCGGGCTGCGTCTAGCTGCAGTAG and Nor-745 ATTGTTCGACAATTACCCTTAG-CAGCCTTGGTGTAGAAGAAACCTCTTT-CACC. Plasmid pKFN-734 was constructed by ligating the 0.4 kb EcoRI-XbaI fragment encoding a synthetic yeast singal-leader fused in-frame to a synthetic insulin precursor gene B(1-29)-AlaAlaLys-A(1-21) from plasmid pLaC212spx3 to the 2.7 kb EcoRI-XbI fragment from pUC-19 (C. Yannisch-Perron et al., Gene 33 (1985), 103–119).

Plasmid pLaC212spx3 is described in Example 3 and in FIG. 6 and 13 of International Patent Application Publication No. WO 89/02463.

Figure 3:
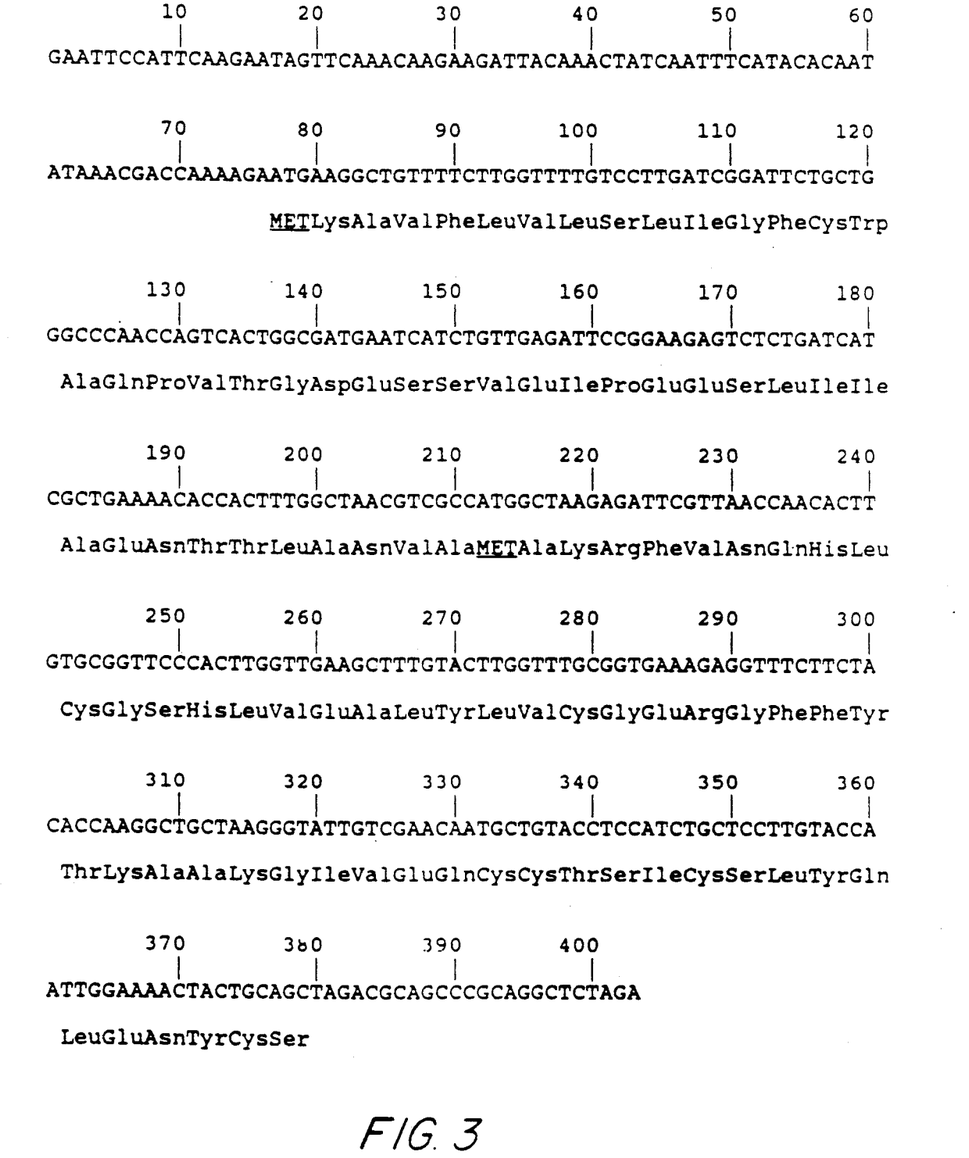
FIG. 3 shows the DNA sequence of the 0.4 kb EcoRI-XbaI fragment from the plasmid pKFN-864.
Figure 4:
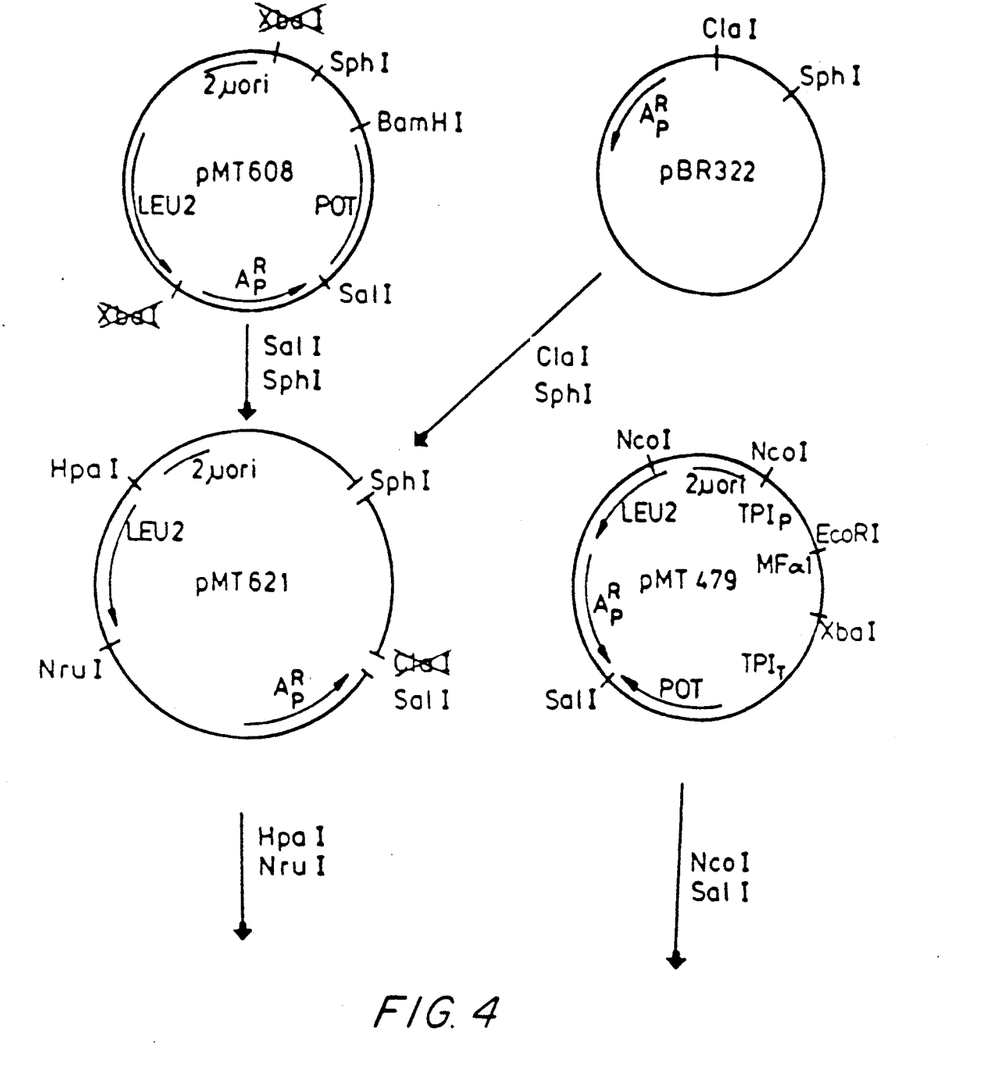
FIG. 4 shows the preparation of the expression plasmid pKFN-866.

The DNA sequence of the 0.4 kb EcoRI-XbaI fragment from pKFN-864 encoding signal-leader-insulin B(1-29, des28 Pro)-AlaAla-Lys-A(1-21, 21 Ser) is given in FIG. 3.

pKFN-864 was cut with EcoRI and XbaI and the 0.5 kb fragment was ligated to the 9.5 kb NcoI-XbaI fragment from pMT636 and the 1.4 kb NcoI-EcoRI fragment from pMT636, resulting in plasmid pKFN-866, see FIG. 4. Plasmid pMT636 was constructed from pMT608 after deletion of the LEU-2 gene and from pMT479, see FIG. 4. pMT608 is described in EP 195 691. pMT479 is described in EP 163 529. pMT479 contains the *Schizosaccharomyces ces pombe* TPI gene (POT), the *S. cerevisiae* triosephosphate isomerase promoter and terminator, TPIP and TPIT (Alber, T. and Kawasaki, G. J. Mol. Appl. Gen. 1 (1982), 419–434). Plasmid pKFN-866 contains the following sequence:

TPI$_P$-signal-leader-insulin B(1-29, des28 Pro)-AlaAlaLys-A(1-21, 21 Ser)-TPI$_T$.

*S. cerevisiae* strain MT663 (E2-7B XE11-36 a/α, ΔtpiΔtpi, pep 4-3/pep 4-3) was grown on YPGaL (1% Bacto yeast extract, 2% Bacto peptone, 2% galactose, 1% lactate) to an O. D. at 600 nm of 0.6.

100 ml of the resulting culture was harvested by centrifugation, washed with 10 ml of water, recentrifuged and resuspended in 10 ml of a solution containing 1.2M sorbitol, 25 mM Na$_2$EDTA pH=8.0, and 6.7 mg/ml dithiotreitol. The suspension was incubated at 30° C. for 15 minutes, centrifuged and the cells resuspended in 10 ml of a solution containing 1.2M sorbitol, 10 mM Na$_2$EDTA, 0.1M sodium citrate, pH=5.8, and 2 mg Novozym ®234. The suspension was incubated at 30° C. for 30 minutes, the cells collected by centrifugation, washed in 10 ml of 1.2M sorbitol and 10 ml of CAS (1.2M sorbitol, 10 mM CaCl$_2$, 10 mM Tris HCL (Tris=Tris(hydroxymethyl)amino methane) pH=7.5) and resuspended in 2 ml of CAS. For transformation 0.1 ml of CAS-resuspended cells were mixed with approximately 1 μg of plasmid pKFN-866 and left at room temperature for 15 minutes. 1 ml of (20% polyethylenglycol 4000, 10 mM CaCl$_2$, 10 mM Tris HCl, pH=7.5) was added and the mixture left for further 30 minutes at room temperature. The mixture was centrifuged and the pellet resuspended in 0.1 ml of SOS (1.2M sorbitol, 33% v/v YPD, 6.7 mM CaCl$_2$, 14 μg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., (Methods in Yeast Genetics, Cold Spring Harbor Laboratory, 1981) containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant KFN-883 was selected for further characterization.

Yeast strain KFN-883 was grown on YPD medium (1% yeast extract, 2% peptone (from Difco Laboratories), and 2% glucose). A 10 ml culture of the strain was shaken at 30° C. to an O.D. at 600 nm of 20. After centrifugation the supernatant was analyzed by HPLC as described (L. Snel et al., Chromatographia 24 (1987), 329–332). The yield was about 0.14 mg/liter of insulin B(1-29, des 28 Pro)-AlaAlaLys-A(1-21, 21 Ser).

The single chain insulin precursor was isolated from the fermentation supernatant by adsorption to an ion exchange column at low pH, desorption at high pH and precipitation of the pool by zinc ions. Transpeptidation of the precursor to [Ser$^{A21}$],des[Pro$^{B28}$], [Thr$^{B30}$-OMe]-human insulin was as follows:

10 mmol (2.35 g) og threonine methylester and glacial acetic acid was dissolved in DMF to give 5 ml, 2.5 ml 76.5% v/v DMF in water was added and 0.5 g of precursor was dissolved in the mixture, which was kept at 12° C.; then 50 mg of trypsin in 1.25 ml 0.05M calcium acetate was added and after 24 hours at 12° C. the reaction mixture was added to 100 ml of acetone for precipitation of the peptides, which were spun down and dried in vacuo.

The isolated insulin analogue ester was purified on a preparative HPLC column using a silica-C18 matrix at acidic pH. Then the purified ester was hydrolyzed in aqueous medium at pH 10 and 25° C. for 24 hours. The [Ser$^{A21}$],des[Pro$^{B28}$]-human insulin formed was precipitated at neutral pH with zinc ions. The precipitate was purified by anion exchange chromatography and subsequently desalted by gel filtration. Yield of lyophilized [Ser$^{A21}$],des[Pro$^{B28}$]-human insulin was 102 mg.

EXAMPLE XIII

Preparation of des[Thr$^{B27}$]-human insulin.

1 g of Zn-free porcine insulin was dissolved in 40 ml of water by adjusting the pH value to 9, and a solution of 50 mg of porcine trypsin in 10 ml of 0.25M ammonium hydrogen carbonate adjusted to pH 9 with ammonia solution was added The solution was then left at 4° C. and after 48 hours a yield of 65% was found by HPLC analysis. The reaction mixture was then gel filtrated at 4° C. on a 5×90 cm column of Sephadex ®G50 superfine in 0.05M ammonium hydrogen carbonate with a flow of 90 ml per hour. Fractions containing the main protein peak were pooled and lyophilized. The yield was 520 mg of des(B23-B30)-human insulin.

A peptide with the sequence Gly-Phe-Phe-Tyr-Pro-Lys-Thr was synthesized on a PAM resin by means of protected symmetrical amino acid anhydrides by means of a peptide synthesis apparatus from Applied Biosystems. Finally, the peptide was cleaved from the resin by anhydrous hydrogen fluoride at 0° C., whereby the remaining protecting groups were simultaneously removed.

200 mg of des(B23-B30)-human insulin and 400 mg of peptide were dissolved in a mixture of 2.40 ml of dimethyl formamide and 1.20 ml of water and the pH-value of the mixture was adjusted 6.5 with triethyl amine. 10 mg of porcine trypsin in 0.20 ml of water was then added and the reaction mixture was left at 20° C. for 4 hours. The reaction was then stopped by addition of 25 ml of 2-propanol and the precipitated proteins were isolated by centrifugation. The drained precipitate was redissolved in 10 ml of 1M acetic acid and applied to a 2.6×20 cm column of Lichroprep ® RP-18 (25–40 μm) previously equilibrated with 0.5 mM hydrochloric acid, 0.1M sodium chloride in 30% (by volume) ethanol. The column was then eluted at 20° C. at a flow of 20 ml per hour with the same buffer but with a linear increase of the ethanol content to 50% over 24 hours. The eluate was monitored for UV-absorption and fractions containing the main protein peak were pooled. The protein was precipitated by dilution with the same volume of water and adjustment of the pH-value to 5.5 with sodium hydroxide solution, and after standing at 4° C. for 1 hour the precipitate was isolated by centrifugation and lyophilization.

The yield was 80 mg of des[ThrB27]-human insulin, which was identified by sequential Edman degradation of the separated vinyl-pyridylated A- and B-chains.

EXAMPLE IV

Formulation of injectable solution.

60 μmoles of a human insulin analogue according to the invention were dissolved in 4 ml of 0.1M HCl and 20 ml of 1.5% m-cresol were added. The solution is now mixed with 40 ml of 4% glycerol and 20 ml of 65 mM disodium hydrogen phosphate, and the pH value was adjusted to 7.3. Finally the solution was adjusted to 100 ml with water and sterilized by filtration.

EXAMPLE V

Evaluation of the degree of association.

A 2.6 cm×88 cm column of Sephadex ®G-75 was equilibrated with 13 mM sodium phosphate buffer pH 7.3 with a flow of 22 ml/hour. By application of des-(octapeptide-B$^{23-30}$)-human insulin, cytochrome C, ribonuclease and mono- and dimeric myoglobin as molecular weight markers a curve representing the molecular weight as a function of the elution volume was drawn.

By application of 1 ml of solution containing 0.6 mM Zn-free human insulin or 0.6 mM insulin analogue and prepared as described in example XII it was found that Zn-free human insulin elutes as a tailing peak with an apparent molecular weight of ≈14 kD and that the analogues prepared as described in the examples VI to X all were eluted as a symmetric peak with an apparent molecular weight of ≈5 kD.

These results indicate that human insulin analogues according to the invention are essential monomeric in solution at pH 7.3, whereas the normal human insulin under the same conditions to a high degree appears as a mixture of dimers and higher oligomers.

EXAMPLE XVI

Evaluation of biological activity.

The biological activity in vitro was determined by measuring the binding affinity to the insulin receptors of isolated rat adipocytes and hepatocytes essentially as described in J. Gliemann, S. Gammeltoft: Diabetologia 10 (1974), 105–113.

The insulin analogues were compared to semisynthetic human insulin, the potency of which was set to 100%, and the results are shown in the table below:

|  | Adipocytes | Hepatocytes |
|---|---|---|
| des[Phe$^{B25}$],des[Thr$^{B30}$]-human insulin | 223% | 201% |
| des[Phe$^{B25}$]-human insulin | 225% | 249% |
| [Asp$^{A21}$]-des[Phe$^{B25}$],des[Thr$^{B30}$]-human insulin | 250% | 242% |

We claim:

1. Human insulin having a deletion of the amino acid at one of the positions B24, B25, B26 or B27.

2. Human insulin having Lys substituted for Pro at position B28.

3. Des[Phe$^{B25}$], des[Thr$^{B30}$]-human insulin.

4. Des[Phe$^{B25}$]-human insulin.

5. [Asp$^{A21}$], des[Phe$^{B25}$], des[Thr$^{B30}$]-human insulin.

6. A pharmaceutical composition comprising a human insulin having a deletion of the amino acid at one of the positions B24, B25, B26 or B27 or a salt thereof together with a pharmaceutically acceptable carrier or diluent.

7. The pharmaceutical composition according to claim 6, wherein said insulin analogue exhibits low solubility at pH 7.3.

8. The pharmaceutical composition according to claim 7, wherein said insulin analogue is essentially monomeric.

9. The pharmaceutical composition according to claim 6, wherein said pharmaceutical composition is formulated as an aqueous solution.

10. The pharmaceutical composition according to claim 6, wherein said pharmaceutical composition is formulated as an aqueous suspension.

11. The pharmaceutical composition according to claim 6, wherein said pharmaceutically acceptable carrier is an aqueous, isotonic solution.

12. The pharmaceutical composition according to claim 9, 10 or 11, wherein said aqueous solution, aqueous suspension or aqueous isotonic solution further comprises zinc ions.

13. The pharmaceutical composition according to claim 9, 10 or 11 wherein said aqueous solution, aqueous suspension or aqueous isotonic solution further comprises a buffer.

14. The pharmaceutical composition of claim 13 wherein said buffer comprises acetate or citrate.

15. The pharmaceutical composition according to claim 9, 10 or 11 wherein said aqueous solution, aqueous suspension or aqueous isotonic solution further comprises a preservative.

16. The pharmaceutical composition of claim 15, wherein said preservative comprises m-cresol, methylparaben or phenol.

17. The pharmaceutical composition of claim 6, wherein said pharmaceutical composition comprises more than one insulin analogue.

18. The pharmaceutical composition according to claim 6, wherein said pharmaceutical composition is formulated for mucosal or transcutaneous administration.

19. The pharmaceutical composition according to claim 6, wherein said pharmaceutical composition is formulated for parenteral administration.

20. A pharmaceutical composition comprising human insulin having Lys substituted for Pro at position B28 or a salt thereof together with a pharmaceutically acceptable carrier or diluent.

21. A method of treating Diabetes mellitus comprising providing to an effected individual a pharmaceutical composition comprising human insulin having a deletion of the amino acid at one of the positions B24, B25, B26 or B27 or a salt thereof together with a pharmaceutically acceptable carrier or diluent.

22. The method according to claim 21, wherein said insulin analogue exhibits low solubility at pH 7.3.

23. The method according to claim 22, wherein said insulin analogue is essentially monomeric.

24. The method according to claim 21, wherein said pharmaceutical composition is formulated as an aqueous solution.

25. The method according to claim 21, wherein said pharmaceutical composition is formulated as an aqueous suspension.

26. The method according to claim 21, wherein said pharmaceutically acceptable carrier is an aqueous, isotonic solution.

27. The pharmaceutical composition according to claim 24, 25 or 26, wherein said aqueous solution, aqueous suspension or aqueous isotonic solution further comprises zinc ions.

28. The pharmaceutical composition according to claim 24, 25 or 26, wherein said aqueous solution, aqueous suspension or aqueous isotonic solution further comprises a buffer.

29. The pharmaceutical composition of claim 28 wherein said buffer comprises acetate or citrate.

30. The pharmaceutical composition according to claim 24, 25 or 26 wherein said aqueous solution, aqueous suspension or aqueous isotonic solution further comprises a preservative.

31. The pharmaceutical composition of claim 30, wherein said preservative comprises m-cresol, methylparaben or phenol.

32. The pharmaceutical composition of claim 21, wherein said pharmaceutical composition comprises more than one insulin analogue.

33. The pharmaceutical composition according to claim 21, wherein said pharmaceutical composition is formulated for mucosal or transcutaneous administration.

34. The method according to claim 21, wherein said pharmaceutical composition is formulated for parenteral administration.

35. A method of treating Diabetes mellitus comprising providing to an effected individual a pharmaceutical composition comprising human insulin having Lys substituted for Pro at position B28 or a salt thereof together with a pharmaceutically acceptable carrier or diluent.

* * * * *

UNITED STATES PATENT AND TRADEMARK OFFICE
CERTIFICATE OF CORRECTION

PATENT NO. : 5,164,366

DATED : November 17, 1992

INVENTOR(S) : Balschmidt et al.

It is certified that error appears in the above-identified patent and that said Letters Patent is hereby corrected as shown below:

Title Page Other Publications

Col. 5, line 19    delete "maybe" and insert "may be"

Col. 9, line 46    delete "mutaqenisation" and insert "mutagenisation"

Col. 11, line 10   delete "...leu 2, cir $\geq$" and insert "...leu 2, cir°"

Col. 14, line 66   delete "ATTGTTCGACAATTACCCTTAG..."
                   and insert "ATTGTTCGACAATACCCTTAG..."

Col. 15, line 24, delete "TPIP" and "TPIT" and insert "TPI$_P$" and "TPI$_T$"

UNITED STATES PATENT AND TRADEMARK OFFICE
CERTIFICATE OF CORRECTION

PATENT NO. : 5,164,366

DATED : December 20, 1989

INVENTOR(S) : Balschmidt et al.

It is certified that error appears in the above-identified patent and that said Letters Patent is hereby corrected as shown below:

Column 19, line 10, delete "pharmaceutical composition", insert --method--

Column 19, line 14, delete "pharmaceutical composition", insert --method--

Column 19, line 18, delete "pharmaceutical composition", insert --method--

Column 19, line 20, delete "pharmaceutical composition", insert --method--

Column 20, line 3, delete "pharmaceutical composition", insert --method--

Column 20, line 6, delete "pharmaceutical composition", insert --method--

Column 20, line 9, delete "pharmaceutical composition", insert --method--

Signed and Sealed this

Twelfth Day of September, 2000

Attest:

Q. TODD DICKINSON

*Attesting Officer*     *Director of Patents and Trademarks*